(12) United States Patent
Khera et al.

(10) Patent No.: US 9,603,846 B2
(45) Date of Patent: Mar. 28, 2017

(54) PROCESS FOR THE PREPARATION OF APIXABAN

(71) Applicant: Cadila Healthcare Limited, Ahmedabad (IN)

(72) Inventors: Brij Khera, Ahmedabad (IN); Kumar Kamlesh Singh, Ahmedabad (IN); Santosh Devidas Diwakar, Ahmedabad (IN); Sunil Dnyaneshwar Narode, Ahmedabad (IN); Hiteshkumar Natwarlal Suthar, Ahmedabad (IN)

(73) Assignee: Cadila Healthcare Limited, Gujarat (IN)

( * ) Notice: Subject to any disclaimer, the term of this patent is extended or adjusted under 35 U.S.C. 154(b) by 0 days.

(21) Appl. No.: 14/950,430

(22) Filed: Nov. 24, 2015

(65) Prior Publication Data

US 2016/0143894 A1 May 26, 2016

(30) Foreign Application Priority Data

Nov. 25, 2014 (IN) .......................... 3729/MUM/2014

(51) Int. Cl.
| | | |
|---|---|---|
| *A61K 31/451* | (2006.01) | |
| *A61K 45/06* | (2006.01) | |
| *C07D 471/04* | (2006.01) | |
| *A61K 31/00* | (2006.01) | |

(52) U.S. Cl.
CPC ............ *A61K 31/451* (2013.01); *A61K 31/00* (2013.01); *A61K 45/06* (2013.01); *C07D 471/04* (2013.01)

(58) Field of Classification Search
None
See application file for complete search history.

(56) References Cited

U.S. PATENT DOCUMENTS

| | | | |
|---|---|---|---|
| 6,919,451 B2 | 7/2005 | Zhou et al. | |
| 6,967,208 B2 * | 11/2005 | Pinto | C07D 211/40 514/303 |
| 6,989,391 B2 | 1/2006 | Pinto et al. | |
| 6,995,172 B2 | 2/2006 | Pinto et al. | |
| 7,005,435 B2 | 2/2006 | Pinto et al. | |
| 7,115,627 B2 | 10/2006 | Pinto et al. | |
| 7,153,960 B2 | 12/2006 | Zhou et al. | |
| 7,338,963 B2 | 3/2008 | Pinto | |
| 7,371,761 B2 | 5/2008 | Pinto et al. | |
| 7,396,932 B2 | 7/2008 | Shapiro et al. | |
| 7,531,535 B2 | 5/2009 | Pinto et al. | |
| 7,691,846 B2 | 4/2010 | Pinto | |
| 7,960,411 B2 | 6/2011 | Pinto | |
| 2007/0203178 A1 | 8/2007 | Malley et al. | |
| 2013/0245267 A1 | 9/2013 | Peddi Reddy et al. | |

FOREIGN PATENT DOCUMENTS

| | | | |
|---|---|---|---|
| CN | 102675314 | 9/2012 | |
| DE | WO 2013174498 A1 * | 11/2013 | ........... A61K 9/2054 |
| WO | 2011/106478 | 9/2011 | |
| WO | 2012/168364 | 12/2012 | |
| WO | 2013/119328 | 8/2013 | |
| WO | 2013/164839 | 11/2013 | |
| WO | 2014/056434 | 4/2014 | |

OTHER PUBLICATIONS

"Investigation on Polymorphs of Apixaban, an Anticoagulant Drug: Study of Phase Transformations and Designing Efficient Process for Their Preparation", Solanki et al., World Journal of Pharmaceutical Sciences, vol. 3(3), pp. 663-677.
"Discovery of 1-(4-Methoxyphenyl)-7-oxo-6-(4-(2-oxopiperidin-1-yl)phenyl)-4,5,6,7-tetrahydro-1*H*-pyrazolo[3,4-*c*]pyridine-3-carboxamide (Apixaban, BMS-562247), a Highly Potent, Selective, Efficacious, and Orally Bioavailable Inhibitor of Blood Coagulation Factor Xa", Pinto et al. J. Med. Chem. 2007, 50, pp. 5339-5356.
"The syntheses and in vitro biotransformation studies of [14C] apixaban, a highly potent, elective, efficacious and orally bioavailable inhibitor of blood coagulation Factor Xa", Maxwell et al., J. Label Compd. Radiopharm 2011, 54, pp. 418-425.
"Development and Validation of Stability Indicating RP-HPLC Method on Core Shell Column For Determination of Degradation and Process Related Impurities of Apixaban—An Anticoagulant Drug", Landge et al., American Journal of Analytical Chemistry, 2015, 6, pp. 539-550.

* cited by examiner

*Primary Examiner* — Heidi Reese
(74) *Attorney, Agent, or Firm* — Nixon & Vanderhye P.C.

(57) ABSTRACT

A crystalline Form N-1 of apixaban substantially free from one or more of: 1-(4-methoxyphenyl)-7-oxo-6-(4-(2-oxopiperidin-1-yl)phenyl)-4,5,6,7-tetrahydro-1H-pyrazolo[3,4-c]pyridine-3-carboxylic acid; 7-oxo-6-(4-(2-oxopiperidin-1-yl)phenyl)-1-phenyl-4,5,6,7-tetrahydro-1H-pyrazolo[3,4-c]pyridine-3-carboxamide; or methyl 1-(4-methoxyphenyl)-7-oxo-6-(4-(2-oxopiperidin-1-yl)phenyl)-4,5,6,7-tetrahydro-1H-pyrazolo[3,4-c]pyridine-3-carboxylate, relative to apixaban by area percentage of HPLC and having a mean particle size equal to or greater than 100 μm.

18 Claims, 3 Drawing Sheets

PROCESS FOR THE PREPARATION OF APIXABAN

CROSS-REFERENCE TO RELATED APPLICATION

This application and claims priority to Indian Application No. 3729/MUM/2014 filed 25 Nov. 2014, the entire contents of which is hereby incorporated by reference.

FIELD OF THE INVENTION

The field of the invention relates to a process for the preparation of apixaban. In particular, the invention relates to a process for the preparation of crystalline Form N-1 of apixaban.

BACKGROUND OF THE INVENTION

The following discussion of the prior art is intended to present the invention in an appropriate technical context and allow its significance to be properly appreciated. Unless clearly indicated to the contrary, however, reference to any prior art in this specification should be construed as an admission that such art is widely known or forms part of common general knowledge in the field.

Chemically, "Apixaban" is known as 4,5,6,7-tetrahydro-1-(4-methoxyphenyl)-7-oxo-6-[4-(2-oxo-1-piperidinyl)phenyl]-1H-pyrazolo[3,4-c]pyridine-3-carboxamide or 1-(4-methoxyphenyl)-7-oxo-6-[4-(2-oxo-1-piperidinyl)phenyl]-4,5,6,7-tetrahydro-1H-pyrazolo[3,4-c]pyridine-3-carboxamide of Formula (I).

International (PCT) Publication No. WO 2003/026652 A1 (the WO '652 A1) discloses the process for the preparation of pyrazole-pyridine derivatives. U.S. Pat. No. 6,967,208, the family equivalent of WO '652 A1 discloses apixaban, has utility as a factor Xa inhibitor, and is developed for oral administration in a variety of indications that require the use of an antithrombotic agent. The US '208 discloses isolation of apixaban using column chromatography. The purity of apixaban obtained by the process disclosed in US '208 is very low and not suitable for pharmaceutical uses. This fact is further confirmed by recent reports in *World Journal of Pharmaceutical Science* Vol. 3(3), Pg. 663-677 (2015) wherein the purity of 90-93% by HPLC was reported.

U.S. Pat. Nos. 7,005,435 B2, 6,989,391 B2, 6,995,172 B2, 7,338,963 B2, 7,371,761 B2, 7,531,535 B2, 7,691,846

2

B2 and 7,960,411 B2 disclose various analogues compounds of apixaban. All the patents are incorporated herein by reference in their entirety.

International (PCT) publication No. WO 2003/049681 A2 and its corresponding U.S. Pat. Nos. 6,919,451 B2 and 7,153,960 B2 disclose process for the preparation of apixaban and other pyrazole-pyridine derivatives.

International (PCT) publication No. WO 2007/001385 A2 and its corresponding U.S. Pat. No. 7,396,932 B2 (the US '932 B2) discloses the process for the preparation of pyrazole-pyridine derivatives as depicted in scheme-1. The US '932 B2 also disclose crystalline Form N-1 and Form H2-2 of apixaban alongwith the unit cell data thereof.

Scheme-1

Wherein, Z is selected from Cl, Br, I, $OSO_2Me$, $OSO_2Ph$, and $OSO_2Ph$-p-Me; ring D is selected from phenyl, 2-fluorophenyl, 3-chlorophenyl, and 4-methoxyphenyl;

$R^{1a}$ is selected from $CH_3$, $CH_2CH_3$, $CH_2CH_2CH_3$, $OCH_3$, $OCH_2CH_3$, $OCH_2CH_2CH_3$, $OCH(CH_3)_2$, $OCH_2CH_2CH_2CH_3$, $OCH(CH_3)CH_2CH_3$, $OCH_2CH(CH_3)_2$, $OC(CH_3)_3$, O-phenyl, $OCH_2$-phenyl, $OCH_2CH_2$-phenyl, and $OCH_2CH_2H_2$-phenyl;

R is selected from Cl, Br, and I; ring A is substituted with 0-1$R^4$; B is $NO_2$.

International (PCT) Publication No. WO 2003/048081 A2 and WO 2003/048158 A1 discloses the process for the preparation of pyrazole-pyridine derivatives by reacting the 3-morpholino-1-(4-nitrophenyl)-5,6-dihydropyridin-2(1H)-one and (Z)-ethyl 2-chloro-2-(2-(4-chlorophenyl)hydrazono)acetate to obtain pyrazole-pyridine derivative as depicted in scheme-2.

Scheme-2

*Journal of Labelled Compounds and Radiopharmaceuticals* Vol. 54 (8) Pg. 418-425 (2011) discloses a nine-step synthesis for the preparation of [$^{14}$C]apixaban with the label in the central lactam ring and three-step synthesis for the preparation of [$^{14}$C]apixaban with the label in the outer lactam ring starting from 4-nitroaniline.

CN 102675314 A discloses the process for the preparation of apixaban by cyclization of p-nitroaniline with 5-chlorovaleroyl chloride or 5-bromovaleroyl chloride; the resulting 1-(4-nitrophenyl)-2-piperidinone underwent dichlorination with phosphorus pentachloride followed elimination; the resulting 3-chloro-5,6-dihydro-1-(4-nitrophenyl)-2(1H)-pyridinone underwent reaction with ethyl (2Z)-chloro[(4-methoxyphenyl)hydrazono]acetate; the resulting ethyl 4,5,6,7-tetrahydro-1-(4-methoxyphenyl)-6-(4-nitrophenyl)-7-oxo-1H-pyrazolo[3,4-c]pyridine-3-carboxylate underwent reduction followed by cyclization with 5-chlorovalaroyl chloride or 5-bromovalaroyl chloride; the resulting intermediate underwent amidation to give apixaban.

*Journal of Medicinal Chemistry* (2007), 50(22), 5339-5356 discloses the process for the preparation of apixaban and other derivatives. The reaction scheme-7 in the reference article discloses the preparation of compound 47a which is outlined herein scheme-3.

Scheme-3

(j) acetyl chloride, NaOH DMC

U.S. Patent Application Publication No. 2007/0203178 A1 discloses crystalline solvates of apixaban viz. dimethyl formamide solvate DMF-5 and formamide solvate Form FA-2 of apixaban characterized by unit cell parameters.

International (PCT) Publication No. WO 2011/0106478 A2 discloses a composition comprising crystalline apixaban particles having a mean particle size equal to or less than about 89 µm and a pharmaceutically acceptable diluent or carrier.

International (PCT) Publication No. WO 2012/0168364 A1 discloses a process for the preparation of apixaban via novel intermediate and crystalline form α of apixaban which is designated as sesquihydrate having water content between about 4.5 and 6.5%. The crystalline form α of apixaban is characterized by x-ray powder diffraction (XRD) and differential scanning calorimetry (DSC).

International (PCT) Publication No. WO 2013/119328 A1 discloses crystalline Form-I, Form-II and Form-III of apixaban.

International (PCT) Publication No. WO 2013/164839 A2 discloses an amorphous form of apixaban and process for the preparation and composition thereof.

U.S. PG-Pub. No. 2013/0245267 A1 discloses an amorphous form of apixaban and process for its preparation.

International (PCT) Publication No. WO 2014/056434 A1 discloses the crystalline form and the amorphous form of apixaban.

*World Journal of Pharmaceutical Science* Vol. 3(3), Pg. 663-677 (2015) discloses the detailed analysis of first synthetic method for the preparation of apixaban, alternative method for the preparation of apixaban, study of impurities during the preparation of apixaban and study of polymorphic forms which is incorporated herein in its entirety.

*American Journal of Analytical Chemistry*, Vol. 6, Pg. 539-550 (2015) discloses development and validation of stability indicating RP-HPLC method on core shell column for determination of degradation and process related impurities of apixaban which is incorporated herein in its entirety.

In view of the above, the present invention provides a process for the preparation of apixaban having higher particle size distribution suitable for formulations with crystalline Form N-1 and having lower level of one or more impurities.

SUMMARY OF THE INVENTION

In one general aspect, there is provided a crystalline Form N-1 of apixaban substantially free from one or more impurities relative to apixaban by area percentage of HPLC and having a mean particle size equal to or greater than 100 µm.

In another general aspect, there is provided a process for the preparation of crystalline Form N-1 of apixaban, the process comprising:

(a) reacting (Z)-ethyl 2-chloro-2-(2-(4-methoxyphenyl)hydrazono)acetate of Formula (V) with 3-morpholino-1-(4-nitrophenyl)-5,6-dihydropyridin-2(1H)-one of Formula (VI) in one or more solvents in the presence of a base optionally in the presence of a phase transfer catalyst to obtain a compound of Formula (IVa);

(V)

(VI)

(IVa)

(b) treating the compound of Formula (IVa) with an acid to obtain a compound of Formula (IV);

(IV)

(c) reducing the compound of Formula (IV) with a reducing agent to obtain a compound (III);

(III)

(d) amidating the compound of Formula (III) with an amidating source in one or more solvents to obtain a compound of Formula (II);

(II)

(e) reacting the compound of Formula (II) with 5-chlorovaleroyl chloride in the presence of a base to obtain compound of Formula (IIB) as a crystalline solid;

(IIB)

(f) cyclizing of compound (IIB) in the presence of a base in one or more solvents to obtain apixaban; and (g) crystallizing the apixaban in one or more solvent to obtain the crystalline Form N-1 of apixaban having a mean particle size equal to or greater than 100 μm.

In another general aspect, there is provided a crystalline Form N-1 of apixaban prepared by the process of the present invention having purity of at least about 99% or more by area percentage of HPLC.

In another general aspect, there is provided a pharmaceutical composition comprising crystalline form N-1 of apixaban having an X-ray powder diffraction pattern comprising peaks expressed in degrees 2θ (±0.2° 2θ) at 8.4°, 12.8°, 13.8°, 16.9°, 18.3°, 21.0°, 22.0°, 24.7°, 25.3°, 26.8° and 32.6°±0.2 2θ, having a mean particle size equal to or greater than 100 μm and one or more pharmaceutically acceptable excipients, diluents and carriers.

DETAILED DESCRIPTION OF THE INVENTION

The present inventors have found that by preparing apixaban in crystalline Form N-1 having mean particle size equal to greater than 100 μm, the formation of impurities can be minimized and better purity and chemical stability can be achieved. The inventors have developed a process for the preparation of apixaban crystalline Form N-1, which exhibit control of impurities and stability under various stress conditions with higher particle size distribution.

In general, the reduction of particle size is achieved by mechanical process of reducing the size of particles which includes any one or more of grinding, milling, micronizing, and trituration or any conventional method known. The most common motivation for decreasing particle size is to increase dissolution. The rate of dissolution of small particles is usually faster than that of large particles because a greater surface area of the drug substance is in contact with the liquid medium. This effect has been highlighted by the superior dissolution rate observed after micronization of sparingly soluble drugs.

But, in contrast to such an approach, the inventors of the present invention provides apixaban with larger particle size which are having ease of preparation and avoid comminution techniques to control particle size. Further, it would be desirable to provide reliable processes for producing apixaban with larger particle size which doesn't affect the bioequivalence. There is provided crystalline Form N-1 of apixaban with better purity and improved stability with larger particle size distribution.

The above and other objects of the present invention are achieved by the process of the present invention, which leads to a process for the preparation of crystalline Form N-1 of apixaban having a mean particle size equal to or greater than 100 μm and which is suitable for formulation.

All ranges recited herein include the endpoints and the terms "about", "from", "to" are to be construed as modifying a value they are applied to such that it is not absolute and includes, to the very least, the degree of expected experimental error, limitation of method or instrument error for a given technique used to measure the value.

As used herein, the term "solution" or "reaction mixture" does not limit to a clear solution only and includes any hazy or opaque mass obtained.

As used herein, the term "obtaining" means isolating the crystalline Form N-1 of apixaban by way of filtration, filtration under vacuum, centrifugation, decantation. The product obtained may be further or additionally dried to achieve the desired moisture values. For example, the product may be dried in a tray drier, dried under vacuum and/or in a Fluid Bed Drier.

The term "composition" used herein means a physical mixture of two or more components.

The term "substantially free" herein means apixaban having impurity-A, impurity-B, impurity-C, impurity-D, impurity-E, impurity-F and impurity-G less than about 0.15% by area percentage of HPLC. In particular, less than about 0.10% by area percentage of HPLC. More particular, not in detectable amount by area percentage of HPLC.

As used herein, "Particle Size Distribution (PSD)" means the cumulative volume size distribution of equivalent spherical diameters as determined by laser diffraction in Malvern Master Sizer 2000 equipment or its equivalent.

As used herein, the term "mean particle size" (also used interchangeably with "VMD" for "volume mean diameter") equal to or greater than a given diameter or being within a given particle size range means that the average of all apixaban particles in the sample have an estimated volume, based on an assumption of spherical shape, greater than or equal to the volume calculated for a spherical particle with a diameter equal to the given diameter.

The term "pharmaceutically acceptable" means that which is useful in preparing a pharmaceutical composition that is generally non-toxic and is not biologically undesirable, and includes that which is acceptable for veterinary use and/or human pharmaceutical use.

The term "pharmaceutical composition" is intended to encompass a drug product including the active ingredient(s), pharmaceutically acceptable excipients that make up the carrier, as well as any product which results, directly or indirectly, from combination, complexation or aggregation of any two or more of the ingredients. Accordingly, the pharmaceutical compositions encompass any composition made by admixing the active ingredient, active ingredient dispersion or composite, additional active ingredient(s), and pharmaceutically acceptable excipients.

The terms herein below are interchangeable and used in the description.

"TEA" refers to triethylamine
"TBA" refers to tert-butyl amine
"DIPA" refers to diisopropyl amine
"DIPEA" refers to diisopropyl ethylamine
"DBU" refers to 1,8-diazabicyclo[5.4.0]undec-7-ene
"DABCO" refers to 1,4-diazabicyclo[2.2.2]octane
"DBN" refers to 1,5-diazabicyclo[4.3.0]non-5-ene In one general aspect, there is provided a crystalline Form N-1 of apixaban substantially free from one or more of: 1-(4-methoxyphenyl)-7-oxo-6-(4-(2-oxopiperidin-1-yl)phenyl)-4,5,6,7-tetrahydro-1H-pyrazolo[3,4-c]pyridine-3-carboxylic acid; 7-oxo-6-(4-(2-oxopiperidin-1-yl)phenyl)-1-phenyl-4,5,6,7-tetrahydro-1H-pyrazolo[3,4-c]pyridine-3-carboxamide; or methyl 1-(4-methoxyphenyl)-7-oxo-6-(4-(2-oxopiperidin-1-yl)phenyl)-4,5,6,7-tetrahydro-1H-pyrazolo[3,4-c]pyridine-3-carboxylate, relative to apixaban by area percentage of HPLC and having a mean particle size equal to or greater than 100 μm.

In general, the crystalline Form N-1 of apixaban having a mean particle size equal to or greater than 100 μm and less than or equal to 500 μm. In particular, greater than 100 μm and less than or equal to 400 μm.

In another general aspect, there is provided a crystalline Form N-1 of apixaban having an X-ray powder diffraction pattern comprising peaks expressed in degrees 2θ (±0.2° 2θ) at 12.8°, 13.8°, 16.9°, 18.3°, 21.0°, 22.0°, and 26.8°±0.2 2θ.

Figure 1:
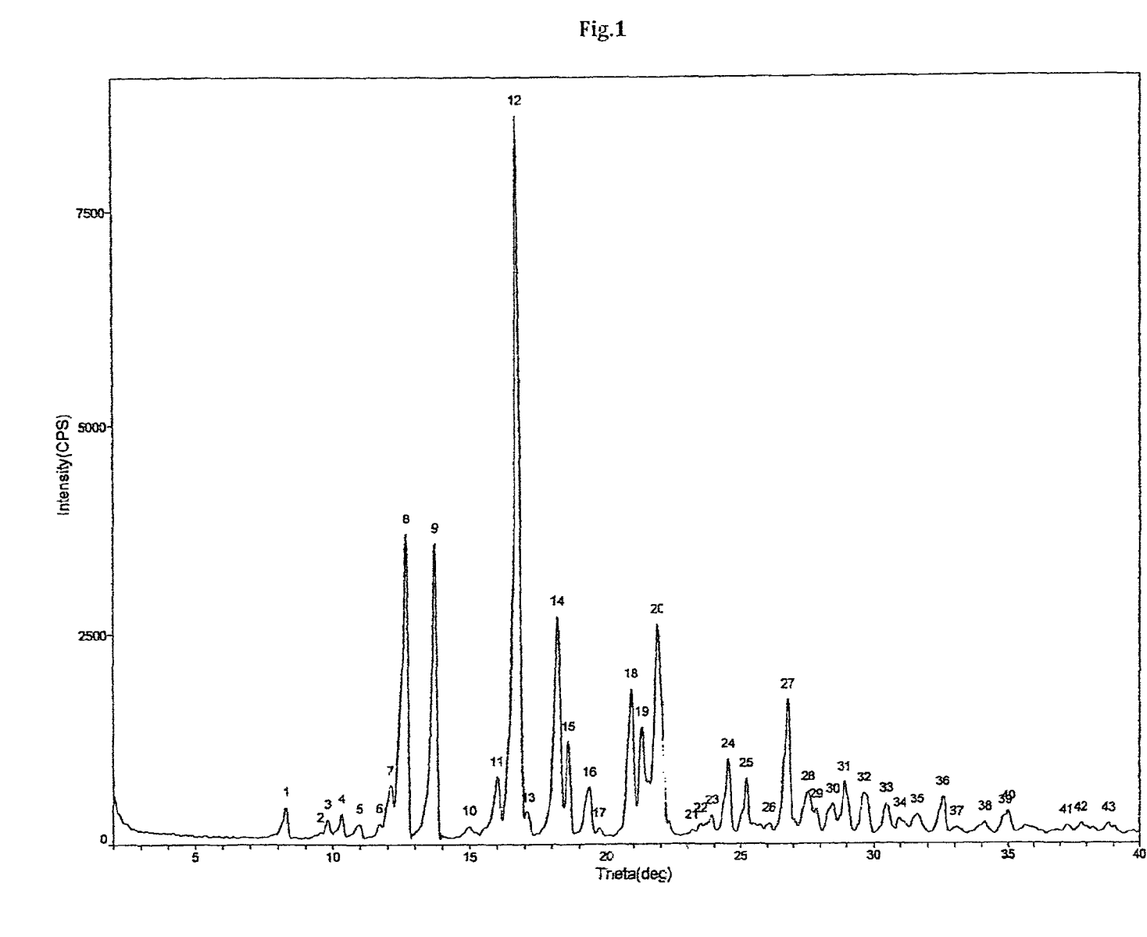
FIG. 1: Illustrates XRPD of crystalline Form N-1 of apixaban (I).

In general, there is provided the crystalline Form N-1 of apixaban having an X-ray powder diffraction pattern comprising peaks expressed in degrees 2θ (±0.2° 2θ) at degrees 2θ (±0.2° 2θ) at 8.4°, 12.8°, 13.8°, 16.9°, 18.3°, 21.0°, 22.0°, 24.7°, 25.3°, 26.8° and 32.6°±0.2 2θ and having X-ray powder diffraction pattern substantially the same as that shown in FIG. 1.

Figure 2:
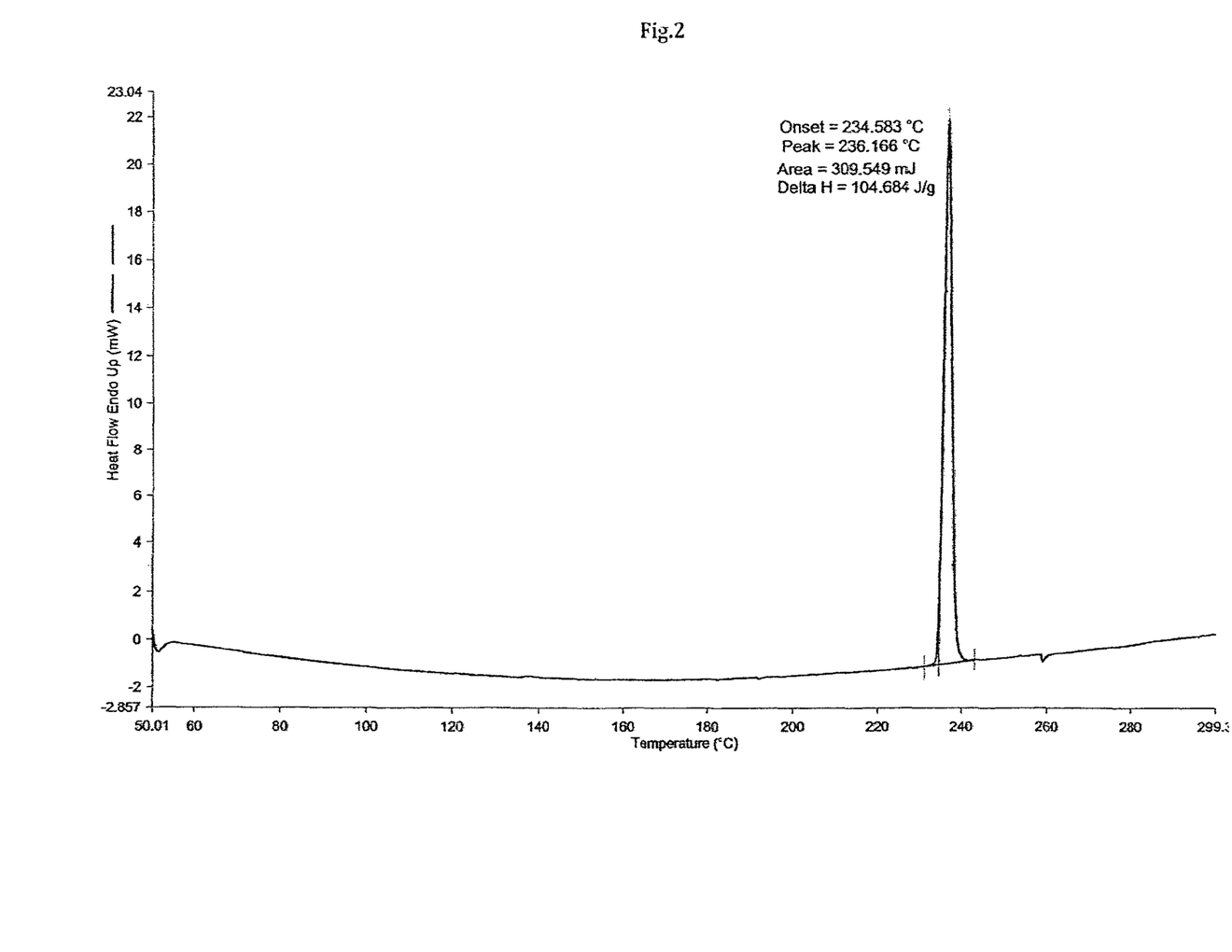
FIG. 2: Illustrates DSC of crystalline Form N-1 of apixaban (I).

In general, there is provided the crystalline Form N-1 of apixaban having a differential scanning calorimetry comprising endothermic peak at about 236±5° C. having onset at about 234±5° C. and differential scanning calorimetry substantially the same as that shown in FIG. 2.

In another general aspect, there is provided a crystalline Form N-1 of apixaban substantially free from one or more impurities.

In general, the impurities of apixaban may be one or more of impurity-A to impurity-G represented by structural formula as herein below:

(Acid Impurity-A)

(Desmethoxy Impurity-B)

(Acetamide Impurity-C)

(Methylester Impurity-D)

(Nitro Impurity-E)

(Amine Impurity-F)

(Chlorocompound Impurity-G)

In general, the impurities of apixaban may be one or more of impurity-A to impurity-G having nomenclature as under:

Acid Impurity-A: 1-(4-methoxyphenyl)-7-oxo-6-(4-(2-oxopiperidin-1-yl)phenyl)-4,5,6,7-tetrahydro-1H-pyrazolo [3,4-c]pyridine-3-carboxylic acid.

Desmethoxy Impurity-B: 7-oxo-6-(4-(2-oxopiperidin-1-yl) phenyl)-1-phenyl-4,5,6,7-tetrahydro-1H-pyrazolo[3,4-c] pyridine-3-carboxamide.

Acetamide Impurity-C: 6-(4-acetamidophenyl)-1-(4-methoxyphenyl)-7-oxo-4,5,6,7-tetrahydro-1H-pyrazolo [3,4-c]pyridine-3-carboxamide.

Methylester Impurity-D: Methyl 1-(4-methoxyphenyl)-7-oxo-6-(4-(2-oxopiperidin-1-yl)phenyl)-4,5,6,7-tetrahydro-1H-pyrazolo[3,4-c]pyridine-3-carboxylate.

Nitro Impurity-E: 1-(4-methoxyphenyl)-6-(4-nitrophenyl)-7-oxo-4,5,6,7-tetrahydro-1H-pyrazolo[3,4-c]pyridine-3-carboxamide.

Amine Impurity-F: 6-(4-aminophenyl)-1-(4-methoxyphenyl)-7-oxo-4,5,6,7-tetrahydro-1H-pyrazolo[3,4-c]pyridine-3-carboxamide.

Chlorocompound Impurity-G: 6-(4-(5-chloropentanamido) phenyl)-1-(4-methoxyphenyl)-7-oxo-4,5,6,7-tetrahydro-1H-pyrazolo[3,4-c]pyridine-3-carboxamide.

In another general aspect, there is provided a composition comprising crystalline Form N-1 of apixaban and one or more of 1-(4-methoxyphenyl)-7-oxo-6-(4-(2-oxopiperidin-1-yl)phenyl)-4,5,6,7-tetrahydro-1H-pyrazolo[3,4-c]pyridine-3-carboxylic acid; 7-oxo-6-(4-(2-oxopiperidin-1-yl) phenyl)-1-phenyl-4,5,6,7-tetrahydro-1H-pyrazolo[3,4-c] pyridine-3-carboxamide; or methyl 1-(4-methoxyphenyl)-7-oxo-6-(4-(2-oxo-piperidin-1-yl)phenyl)-4,5,6,7-tetrahydro-1H-pyrazolo[3,4-c]pyridine-3-carboxylate in an amount relative to apixaban less than about 0.15% by weight by area percentage of HPLC.

In general, the composition comprising crystalline Form N-1 of apixaban wherein the apixaban has a purity of greater than or equal to 99% by weight, and 1-(4-methoxyphenyl)-7-oxo-6-(4-(2-oxopiperidin-1-yl)phenyl)-4,5,6,7-tetrahydro-1H-pyrazolo[3,4-c]pyridine-3-carboxylic acid present in an amount relative to apixaban less than about 0.10% by weight by area percentage of HPLC.

In general, the composition comprising crystalline Form N-1 of apixaban wherein the apixaban has a purity of greater than or equal to 99% by weight, and 7-oxo-6-(4-(2-oxopiperidin-1-yl)phenyl)-1-phenyl-4,5,6,7-tetrahydro-1H-pyrazolo[3,4-c]pyridine-3-carboxamide present in an amount relative to apixaban less than about 0.10% by weight by area percentage of HPLC.

In general, the composition comprising crystalline Form N-1 of apixaban wherein the apixaban has a purity of greater than or equal to 99% by weight, and methyl 1-(4-methoxyphenyl)-7-oxo-6-(4-(2-oxopiperidin-1-yl)phenyl)-4,5,6,7-tetrahydro-1H-pyrazolo[3,4-c]pyridine-3-carboxylate present in an amount relative to apixaban less than about 0.10% by weight by area percentage of HPLC.

In general, the composition as herein above comprising crystalline Form N-1 of apixaban wherein the apixaban has a purity of greater than or equal to 99.8% by weight by area percentage of HPLC.

In another general aspect, there is provided a crystalline Form N-1 of apixaban prepared by a process comprising:

(a) reacting (Z)-ethyl 2-chloro-2-(2-(4-methoxyphenyl)hydrazono)acetate of Formula (V) with 3-morpholino-1-(4-nitrophenyl)-5,6-dihydropyridin-2(1H)-one of Formula (VI) in one or more solvents in the presence of a base optionally in presence of a phase transfer catalyst to obtain a compound of Formula (IVa);

(V)

(VI)

(b) treating the compound of Formula (IVa) with an acid to obtain a compound of Formula (IV);

(IV)

(c) reducing the compound of Formula (IV) with a reducing agent to obtain a compound of Formula (III);

(III)

(d) amidating the compound of Formula (III) with an amidating source in one or more solvents to obtain a compound of Formula (II);

(II)

(e) reacting the compound of Formula (II) with 5-chlorovaleroyl chloride in the presence of a base to obtain a compound of Formula (IIB) as a crystalline solid;

(IIB)

(f) cyclizing the compound of Formula (IIB) in the presence of a base in one or more solvents to obtain apixaban; and
(g) crystallizing the apixaban in one or more solvents to obtain the crystalline Form N-1 of apixaban having a mean particle size equal to or greater than 100 μm.

In another general aspect, the process further comprises converting the crystalline Form N-1 of apixaban obtained to an amorphous form.

The embodiments of the process involves reacting (Z)-ethyl 2-chloro-2-(2-(4-methoxyphenyl)hydrazono)acetate of Formula (V) with 3-morpholino-1-(4-nitrophenyl)-5,6-dihydropyridin-2(1H)-one of Formula (VI) in the presence of a base in one or more solvents.

In general, the solvents comprise one or more of water, methanol, ethanol, isopropanol, n-butanol, ethyl acetate, isopropyl acetate, butyl acetate, acetone, methylethyl ketone, methylisobutyl ketone, acetonitrile, dimethylformamide, dimethylacetamide, dimethylsulfoxide, N-methyl pyrrolidone, tetrahydrofuran, 2-methyl tetrahydrofuran, toluene, xylene, methylene dichloride, and ethylene dichloride or mixture thereof. In particular, ethyl acetate and dimethylformamide may be used to obtain the compound of Formula (IVa).

In general, the base is selected from one or more of sodium hydroxide, potassium hydroxide, lithium hydroxide, sodium carbonate, potassium carbonate, lithium carbonate, cesium carbonate, sodium bicarbonate, potassium bicarbonate, sodium hydride, potassium hydroxide, sodium methoxide, sodium ethoxide, potassium tert-butoxide, ammonia, TEA, DIPA, DEA, DIPEA, N-methyl morpholine, DBU, DABCO, and DBN. In particular, the TEA or DIPEA may be used.

In general, the reaction may be optionally performed in the presence of an alkali metal halide such as sodium iodide or potassium iodide.

In another general aspect, the reaction of (Z)-ethyl 2-chloro-2-(2-(4-methoxyphenyl)hydrazono)acetate of Formula (V) with 3-morpholino-1-(4-nitrophenyl)-5,6-dihydropyridin-2(1H)-one of Formula (VI) may be optionally performed in a biphasic solvent medium in the presence of a base and a phase transfer catalyst to obtain the compound of Formula (IVa). The solvent medium comprises one or more of water-toluene, water-xylene, water-ethylacetate, methanol-cyclohexane, and water-methylene dichloride.

In general, the phase transfer catalyst comprises one or more of tetrabutyl ammonium bromide (TBAB), tetrabutyl ammonium iodide (TBAI), benzyl triethyl ammonium chloride (TEBAC), polyethylene Glycol (PEG-200, 400, 600, 800, 1000), crown ethers such as 12-crown-4, 15-crown-5, 18-crown-6, dibenzo-18-crown-6, and diaza-18-crown-6. In particular, TBAB may be used as phase transfer catalyst.

The compound of Formula (IVa) is treated with an acid comprises one or more of hydrochloric acid, nitric acid, hydrobromic acid, sulfuric acid, acetic acid, and phosphoric acid to obtain compound of Formula (IV). The reaction may be performed in solvent selected from alcohols, esters or ketones as disclosed herein above.

In general, the reducing agent comprises one or more of Raney Nickel, Pd/C, Pt/C, Platinum oxide, Fe—HCl, Fe—NH$_4$Cl, Sn—HCl, and Na$_2$S$_X$. In particular, Fe—NH$_4$Cl may be used.

In general, the reduction of compound of Formula (IV) is performed in one or more solvents selected from of methanol, ethanol, isopropanol, ethyl acetate, isopropyl acetate, acetonitrile, acetone, methylene dichloride, tetrahydrofuran, and water or mixture thereof. In particular, water, methanol, ethanol, acetone, ethyl acetate, methylene dichloride, water-methanol or water-ethanol, water-acetone, methanol-tetrahydrofuran may be used.

In general, the amidating source comprises contacting the ester compound of Formula (III) with a formamide or ammonia and a base in one or more solvents.

The formamide comprises one or more of N-ethyl-formamide, N-methyl-formamide, N,N-dimethylformamide and formamide. The base comprises one or more of sodium carbonate, potassium carbonate, cesium carbonate, sodium bicarbonate, potassium bicarbonate, sodium hydride, potassium hydride, sodium hydroxide, potassium hydroxide, lithium hydroxide, sodium methoxide, sodium ethoxide, and potassium tert-butoxide. In particular, sodium methoxide may be used.

Alternatively, the amidation is also done using ammonia in the presence of one or more solvents comprises alcohols selected from methanol, ethanol, isopropanol, and butanol; ketones selected from acetone, methyl ethyl ketone, and methyl isobutyl ketone; esters selected from ethyl acetate, isopropyl acetate, and butyl acetate may be used.

The embodiments of the process further comprises, reacting the compound of Formula (II) with 5-chlorovaleroyl chloride in the presence of a base to obtain compound of Formula (IIB). Alternatively, the amide compound of Formula (II) may also be reacted with 5-bromovaleroyl chloride in the presence of a base to obtain compound of Formula (IIA) in one or more solvents.

(IIA)

In general, the base comprises one or more of sodium hydroxide, potassium hydroxide, lithium hydroxide, sodium carbonate, potassium carbonate, lithium carbonate, sodium bicarbonate, potassium bicarbonate, sodium hydride, potassium hydroxide, sodium methoxide, sodium ethoxide, potassium tert-butoxide, ammonia, TEA, DIPA, DEA, DIPEA, DBU, DABCO, and DBN. In particular, TEA or DIPEA may be used.

In general, the solvent for the reaction of 5-chlorovaleroyl chloride or 5-bromovaleroyl chloride comprises one or more of methanol, ethanol, isopropanol, n-butanol, ethyl acetate, isopropyl acetate, butyl acetate, acetone, methylethyl ketone, methylisobutyl ketone, acetonitrile, dimethylformamide, dimethylacetamide, dimethylsulfoxide, N-methyl pyrrolidone, tetrahydrofuran, 2-methyl tetrahydrofuran, toluene, xylene, methylene dichloride, and ethylene dichloride. In particular, methylene dichloride may be used.

The embodiment of the process comprises obtaining the compound of Formula (IIA) or (IIB) by addition of water to the reaction mixture. The compounds of Formula (IIA) or (IIB) may be obtained by filtration of the reaction mixture.

In general, the crystalline solid compound of Formula (IIB) may be cyclized in presence of base in one or more solvents to obtain apixaban. In general the base comprises one or more of sodium carbonate, potassium carbonate, cesium carbonate, sodium bicarbonate, potassium bicarbonate, sodium hydride, potassium hydride, sodium hydroxide, potassium hydroxide, lithium hydroxide, sodium methoxide, sodium ethoxide, potassium tert-butoxide and sodium hydride. In particular, sodium hydroxide or sodium hydride may be used.

In particular, the solvent comprises one or more of dimethylformamide, dimethyl acetate, dimethylsulfoxide, N-methylpyrrolidone, acetonitrile, tetrahydrofuran, and 1,4-dioxane. In particular, dimethylacetamide may be used.

In general, the apixaban obtained in step (e) is crystallized in one or more solvents. The solvent comprises one or more of water, alcohols selected from methanol, ethanol, isopropanol, 2-propanol, 1-butanol, t-butyl alcohol, 1-pentanol, and 2-pentanol; esters selected from ethyl acetate, propyl acetate, isopropyl acetate, t-butyl acetate, and isobutyl acetate; ethers selected from diethyl ether, diisopropyl ether, methyl tert-butyl ether, tetrahydrofuran, 2-methyl tetrahydrofuran, and dioxane; ketones selected from acetone, butanone, 2-pentanone, 3-pentanone, methylbutyl ketone, and methyl isobutyl ketone; halogenated hydrocarbon selected from methylene dichloride, ethylene dichloride, carbon tetrachloride and chlorobenzene; polar aprotic solvent selected from dimethylformamide, dimethylsulfoxide, and N-methylpyrrolidone; and acetonitrile, or mixture thereof.

In general, the process comprises crystallizing apixaban in one or more solvents, removing the solvents, optionally adding one or more anti-solvents, and isolating the crystalline Form N-1 of apixaban. The stirring RPM (rotation per minute) may be with slow stirring rate, in particular in the range of 60 to 100. The cooling should be at the rate of 20° C. per hour i.e. within one hour, reaction mixture may be cooled to 25° C. and gradually to 10° C. thereafter. The apixaban may be obtained as crystalline solid by conventional technique.

The crystalline Form N-1 of apixaban obtained may be crystallized in one or more of solvents selected from alcohols comprising methanol, ethanol, isopropanol, and butanol; esters comprising ethyl acetate, isopropyl acetate, n-propyl acetate, and butyl acetate; ketones comprising acetone, methyl ethyl ketone, and methyl isobutyl ketone; dimethylformamide, dimethylacetamide, dimethylsulfoxide or mixture thereof to achieve the higher particle size. The crystallization may include heating apixaban at about 70-75° C. while maintaining the stirring rate from 60 to 100 RPM followed by cooling within 1 hour to 0-10° C. The particles thus obtained upon filtration were washed with solvent of recrystallization and dried for 6-8 hours at atmospherically. The product thus obtained may be sieved from 60 Mesh to achieve higher particle size.

In another general aspect, there is provided a crystalline Form N-1 of apixaban prepared by the process of the present invention having purity of at least about 99% by area percentage of HPLC. In particular, the crystalline Form N-1 of apixaban having a purity of at least about 99.5% or more, or having purity of at least about 99.8% or more, or having purity of at least about 99.9% or more by area percentage of HPLC.

In another general aspect, there is provided a crystalline form N-1 of apixaban prepared by the process of the present invention having mean particle size equal to greater than of 100 μm.

In another general aspect, there is provided a pharmaceutical composition comprising apixaban having a purity of greater than or equal to 99% by weight; one or more of 1-(4-methoxyphenyl)-7-oxo-6-(4-(2-oxopiperidin-1-yl)phenyl)-4,5,6,7-tetrahydro-1H-pyrazolo[3,4-c]pyridine-3-carboxylic acid; 7-oxo-6-(4-(2-oxopiperidin-1-yl)phenyl)-1-phenyl-4,5,6,7-tetrahydro-1H-pyrazolo[3,4-c]pyridine-3-carboxamide; or methyl 1-(4-methoxyphenyl)-7-oxo-6-(4-(2-oxopiperidin-1-yl)phenyl)-4,5,6,7-tetrahydro-1H-pyrazolo[3,4-c]pyridine-3-carboxylate in an amount relative to apixaban less than about 0.15% by weight by area percentage of HPLC; and one or more pharmaceutically acceptable excipients, diluents and carriers.

In another general aspect, there is provided a pharmaceutical composition comprising crystalline form N-1 of apixaban having an X-ray powder diffraction pattern comprising peaks expressed in degrees 2θ (±0.2° 2θ) at 8.4°, 12.8°, 13.8°, 16.9°, 18.3°, 21.0°, 22.0°, 24.7°, 25.3°, 26.8° and 32.6°±0.2 2θ and having a mean particle size equal to or greater than 100 μm and one or more pharmaceutically acceptable excipients, diluents and carriers.

Powder X-ray diffraction of apixaban and intermediates thereof can be obtained under following conditions.

(i) Characterization by Powder X-Ray Diffraction

The X-ray powder diffraction spectrum was measured using X-Ray Diffractometer, D/Max-2200/PC Make or equivalent and having CuKα source.

(ii) Characterization by Differential Scanning Calorimetry (DSC)

Analytical method: Differential scanning calorimetric analysis was performed using a Perkin Elmer Diamond DSC control unit and a DSC 300° C. differential scanning calorimeter. 2-5 mg samples were placed in crimped aluminum pans and heated from 50° C. to 300° C. in a liquid nitrogen atmosphere at a heating rate of 10° C./minute. Zinc-Indium was used as the standard substance.

Having described the invention with reference to certain preferred embodiments, other embodiments, reaction conditions, temperature control and solvent system may become apparent to one skilled in the art from consideration of the examples provided herein after.

EXAMPLES

Preparation of Starting Materials

Example-1

Preparation of (Z)-ethyl 2-chloro-2-(2-(4-methoxyphenyl)hydrazono)acetate (VI)

In first 500 mL 3-neck round bottom flask equipped with mechanical stirrer, thermometer and addition funnel, water (85 mL) and p-anisidine (25 gm) were added at 25° C. to 30° C. The reaction mixture was cooled to 0° C. to 5° C. Con. HCl (50 mL) was added to the reaction mixture and stirred for 15 min.

In second 500 mL 3-neck round bottom flask equipped with mechanical stirrer, thermometer and addition funnel, water (43 mL) and sodium nitrite 16.9 g were added at 25° C. to 30° C. The reaction mixture was cooled to 0° C. to 5° C. and above prepared reaction mixture was added to it. The reaction mixture was stirred for 1 hour at 0-5° C.

In third 500 mL 3-neck round bottom flask equipped with mechanical stirrer, thermometer and addition funnel, water (81 mL) and sodium acetate (38.4 g) were added at room temperature. The reaction mixture was cooled to 0° C. to 5° C. and ethyl 2-chloroaceto acetate (33.5 gm) and ethyl acetate (162.5 mL) were added and stirred for 15 min. The above reaction mixture prepared in second 500 mL 3-neck round bottom flask was added at 0° to 5° C. and stirred for 30 min. The reaction mixture was warmed to 25° C. to 30° C. for 30 mins. The separated organic layer was charcoalized and filtered. The filtrate was distilled to remove ethyl acetate under vacuum at 45° C. to 50° C. and cooled to 25° C. Methanol (50 mL) was added and cooled to 0° C. to 5° C. The reaction mixture was stirred for 30 mins and filtered. The solid obtained was washed with methanol and dried under vacuum at 45° C. to 50° C. to obtain 28.2 g of titled compound.

Example-2

Preparation of 3-morpholino-1-(4-nitrophenyl)-5,6-dihydropyridin-2(1H)-one (VII)

(A) Preparation of 5-bromo-N-(4-nitrophenyl)pentanamide

In 1 L 3-neck round bottom flask equipped with mechanical stirrer, thermometer and addition funnel, 4-nitroaniline (50 gm) and tetrahydrofuran (250 mL) were taken at 25° C. and cooled to 0° to 5° C. 5-bromovalaroyl chloride (101.09 gm) and a solution of triethylamine (65.81 gm) in tetrahydrofuran (50 mL) were added at 0° C. to 5° C. The reaction mixture was stirred at 25° C. for 1-2 hours and cooled to 0° C. to 5° C. The reaction mixture was stirred at 5° C. to 10° C. for 1 hour and water (1500 mL) was added. The reaction mixture was filtered and the wet-cake was washed with water and dried at 55° C. to 60° C. under vacuum for 8 hours to obtain 108.2 g of 5-bromo-N-(4-nitrophenyl)pentamide.

The reaction may be repeated to obtain 5-chloro-N-(4-nitrophenyl)pentamide by replacing 5-bromovalaroyl chloride with 5-chlorovalaroyl chloride.

(B) Preparation of 1-(4-nitrophenyl)piperidin-2-one

In 3 L 4-neck round bottom flask equipped with mechanical stirrer, thermometer and addition funnel, 60% sodium hydride (23.9 gm) and THF (450 mL) were added at 25° C. and stirred for 15 min to obtain reaction mixture. The reaction mixture was cooled to 0° C. to 5° C. and 5-bromo-N-(4-nitrophenyl)pentamide (100 gm) was added. The reaction mixture was stirred for 30 mins. Water (1250 mL) and MDC (750 mL) were added at 5° C. to 10° C. and warmed to 25° C. and stirred for 1 hour. The reaction mixture was filtered and the filtrate was distilled under vacuum at 45° C. to 50° C. Toluene (100 mL) was added and stirred for 30 min. The reaction mixture was filtered and washed with toluene. The product was dried under vacuum at 50° C. to 55° C. for 6-8 hours to obtain 52.5 gm of 1-(4-nitrophenyl)piperidin-2-one.

(C) Preparation of 3-morpholino-1-(4-nitrophenyl)-5,6-dihydropyridin-2(1H)-one

In 3 L 4-neck round bottom flask equipped with mechanical stirrer, thermometer and addition funnel, methylene dichloride (120 mL) and $PCl_5$ (85.15 gm) were added at 25° C. The reaction mixture was stirred for 15 min and cooled to 0° C. to 5° C. A solution of 1-(4-nitrophenyl)piperidin-2-one (30 gm) in methylene dichloride (120 ml) was added and stirred for 30 min. The reaction mixture was raised to 25° C. to 30° C., stirred for 2 hours and cooled to 0° C. to 5° C. Water (600 mL) was added and stirred to separate the layer. The separated methylene dichloride was dried over anhydrous sodium sulphate and distilled under vacuum at 45° C. to 50° C. Morpholine (156 mL) was added and stirred for 30 min followed by heating at 125-130° C. for 30 min. The reaction mixture was cooled to 70° C. to 75° C. and distilled to remove excess morpholine under vacuum at 70° C. to 75° C. and cooled to 55° C. to 60° C. Methanol (120 mL) and water (60 mL) was added at 55° C. to 60° C. and cooled to 25° C. to 30° C. The reaction mixture was stirred for 30 mins and filtered. The solid was washed with water and dried at 50° C. to 55° C. under vacuum to obtain 16 gm of 3-morpholino-1-(4-nitrophenyl)-5,6-dihydropyridin-2(1H)-one (VII).

Preparation of Apixaban

Example-3

Preparation of ethyl 1-(4-methoxyphenyl)-7a-morpholino-6-(4-nitrophenyl)-7-oxo-3a,4,5,6,7,7a-hexahydro-1H-pyrazolo[3,4-c]pyridine-3-carboxylate (Va)

In 500 mL 3-neck round bottom flask equipped with mechanical stirrer, thermometer and addition funnel, 3-morpholino-1-(4-nitrophenyl)-5,6-dihydropyridin-2(1H)-one (VI) (30 g, 98.91 mmol) and (Z)-ethyl 2-chloro-2-(2-(4-methoxyphenyl)hydrazono)acetate (V) (30.36 g, 118.3 mmol) and triethylamine (21.02 g, 207.73 mmol) were suspended in ethyl acetate (150 mL) at 75° C. to 80° C. The reaction was monitored by HPLC. The reaction mixture was cooled to 25° C. to 35° C. The water (30 mL) was added and stirred for 30 min. The yellow solid was filtered and washed with ethyl acetate (30 mL). The product was dried at 60° C. under vacuum till constant weight.

Example-4

Preparation of ethyl 1-(4-methoxyphenyl)-6-(4-nitrophenyl)-7-oxo-4,5,6,7-tetrahydro-1H-pyrazolo[3,4-c]pyridine-3-carboxylate (V)

In 500 mL 3-neck round bottom flask equipped with mechanical stirrer, thermometer and addition funnel, the compound (Va) (50 g, 95.5 mmol) was suspended in isopropyl alcohol, conc. HCl (12.5 mL) was added. The reaction mass was heated at 75-80° C. for 3 h under stirring. The progress of the reaction was monitored by HPLC. The reaction mass was cooled and pale yellow product was filtered, washed with isopropyl alcohol (50 mL). The product was dried at 60° C. under vacuum till constant weight.

Example-5

Preparation of ethyl 6-(4-aminophenyl)-1-(4-methoxyphenyl)-7-oxo-4,5,6,7-tetrahydro-1H-pyrazolo[3,4-c]pyridine-3-carboxylate (IV)

In 1 L 3-neck round bottom flask equipped with mechanical stirrer, thermometer and addition funnel, ethyl 1-(4-methoxyphenyl)-6-(4-nitrophenyl)-7-oxo-4,5,6,7-tetrahydro-1H-pyrazolo[3,4-c]pyridine-3-carboxylate (38 g, 87.07 mmol), iron (19.44 g, 382 mmol), ammonium chloride (10.25 g, 191.6 mmol) was suspended in methanol (418 mL) and water (152 mL) were added at 25-30° C. The reaction mixture was heated at 65° C. to 70° C. for 3 hours. The progress of the reaction was monitored by HPLC. The reaction mixture was cooled to 25° C. to 30° C. and methylene dichloride (304 mL) was added. The reaction mixture was filtered and washed with methylene dichloride. The methylene chloride layer was separated and distilled under vacuum at 45° C. to 50° C. The residue was stirred with cyclohexane (190 mL), filtered and washed with cyclohexane (76 mL). The product was dried at 60° C. under vacuum to obtain constant weight of title compound.

Example-6

Preparation of 6-(4-aminophenyl)-1-(4-methoxyphenyl)-7-oxo-4,5,6,7-tetrahydro-1H-pyrazolo[3,4-c]pyridine-3-carboxamide (III)

Compound (IV) (30 g) and 18-20% methanolic ammonia (450 mL) was heated at 70° C. in autoclave for 12 hours or in methanol 300 ml at 70° C. under 6-7 kg pressure of ammonia. The progress of the reaction was monitored by HPLC. The methanol was evaporated under vacuum at 50° C. and residue was stirred with methanol (45 mL) for 1 hour. The product was filtered, washed with 30 ml of methanol and wet-cake was dried at 60° C. under vacuum till constant weight.

Example-7

Preparation of Compound (IIA)

In 250 mL 3-neck round bottom flask equipped with mechanical stirrer, thermometer and addition funnel, Compound (III) (6 g, 15.9 mmol.) and pyridine (3.77 g, 47.76 mmol) in dichloromethane (60 mL) was stirred at 25-35° C. 5-chlorovaleroyl chloride (6.16 g, 39.75 mmol) in methylene dichloride (12 mL) in 30-40 min. The reaction mass is stirred for 3 h at 25-35° C. The progress of the reaction was monitored by HPLC. Methylene dichloride was distilled below 50° C. and degassed for 30 min at 45-50° C. The reaction mass was cooled to 30-35° C. and water (42 mL) and ethyl acetate (18 mL) were added, stirred for 30 min and the product was filtered and washed with water (12 mL) followed by ethyl acetate (12 mL) and suck dried. The wet-cake was suspended in ethyl acetate (30 mL), stirred for 30 min at reflux and cooled to 25-30° C. and filtered. The product of formula (IIA) was dried at 60° C. till constant weight.

Example-8

Preparation of Compound (IIA)

In 250 mL 3-neck round bottom flask equipped with mechanical stirrer, thermometer and addition funnel, compound (III) (24 g, 63.63 mmol) and 5-chlorovaleroyl chloride (24.66 g, 159.1 mmol) in ethyl acetate (168 mL) was stirred at 25-35° C. TEA (19.3 g, 190.1 mmol) in ethyl acetate (24 mL) was added and the reaction mass was stirred for 3 hours at 60-65° C. The progress of reaction was monitored by HPLC and cooled. Water (96 mL) was added and the white solid was filtered and washed with ethyl acetate (48 mL) and suck dried. The wet cake was suspended in ethyl acetate (120 mL) and stirred for 30 min at 75-80° C., cooled and filtered. The product of formula (IIA) was dried at 60° C. till constant weight.

Example-9

Preparation of Apixaban (I)

In 250 mL 3-neck round bottom flask equipped with mechanical stirrer, thermometer and addition funnel, compound (IIA) (1 g, 2.01 mmol) in dimethylacetamide (5 mL) and 60% NaH (145 mg, 6.02 mmol) were stirred at 0-5° C. for 2 hours. The progress of the reaction was monitored by HPLC. Methanol (3 mL), methylene dichloride (12 mL) and water (5 mL) were added. The reaction mixture was heated to 30-40° C. and the separated aqueous layer was extracted with methylene dichloride (3 mL). The combined organic layer was washed with water (5 mL). The organic layer was separated and distilled under vacuum at 45-50° C. The residue was stirred at reflux for 1 hour with methanol (5 mL), filtered and washed with methanol. The product was dried at 60° C. under vacuum till constant weight.

Example-10

Preparation of Apixaban (I)

In 250 mL 3-neck round bottom flask equipped with mechanical stirrer, thermometer and addition funnel, compound (IIA) (25 g, 50.4 mmol) in dimethylacetamide (125 mL) and NaOH (6.05 mg, 151.22 mmol) dissolved in methanol (50 mL) were stirred at 25-30° C. for 2 hours. The progress of the reaction was monitored by HPLC. Methylene dichloride (300 mL) and water (125 mL) were added. The reaction mixture was heated to 30-40° C. and the separated aqueous layer was extracted with methylene dichloride (75 mL). The combined organic layer was washed with water (125 mL). The organic layer was separated and distilled under vacuum at 45-50° C. The residue was stirred at reflux for 1 hour with methanol (125 mL), filtered and washed with methanol. The product was dried at 60° C. under vacuum till constant weight.

Example-11

Purification of Apixaban (I)

In 250 mL 3-neck round bottom flask equipped with mechanical stirrer, thermometer and addition funnel, apixaban (16 g, 34.81 mmol) was suspended in mixture of dimethylsulfoxide-methanol (4:6) at 25-30° C. The suspension was heated to 70-75° C. to obtain the clear solution. The reaction mixture was cooled gradually to 25-30° C. and then further cooled to 0-5° C. The off-white product was filtered and washed with methanol (16 mL). The wet-cake was dried at 60° C. till constant weight to obtain pure Apixaban having purity 99.8%.

(XRD: FIG. 1, DSC: FIG. 2)
PSD D(10): 28.5 μm; D(50): 105.0 μm; D(90): 229.1 μm.

Preparation of Amorphous Apixaban

Example-12

100 mg (0.217 m mol) of apixaban and 15 mL methanol were taken in round bottom flask at 25-30° C. The reaction mixture was heated at 45-50° C. to obtain clear solution. 100 mg of PVP-K30 polymer was added and stirred at 45-50° C. for 2 hours. The reaction mixture was distilled under vacuum at 60-65° C. The product was dried under vacuum at 55-60° C. to obtain 120 mg amorphous apixaban.

Example-13

100 mg (0.217 mmol) of apixaban and 15 mL methanol were taken in round bottom flask at 25-30° C. The reaction mixture was heated at 45-50° C. to obtain clear solution. 200 mg of PVP-K30 polymer was added and stirred at 45-50° C. for 2 hours. The reaction mixture was distilled under vacuum at 60-65° C. The product was dried under vacuum at 55-60° C. to obtain 155 mg amorphous apixaban.

Example-14

50 mg (0.108 mmol) of apixaban and 10 mL methanol were taken in round bottom flask at 25-30° C. The reaction mixture was heated at 45-50° C. to obtain clear solution. 200 mg of PVP-K30 polymer was added and stirred at 45-50° C. for 2 hours. The reaction mixture was distilled under vacuum at 60-65° C. The product was dried under vacuum at 55-60° C. to obtain 125 mg amorphous apixaban.

Example-15

40 mg (0.087 mmol) of apixaban and 10 mL methanol were taken in round bottom flask at 25-30° C. The reaction mixture was heated at 45-50° C. to obtain clear solution. 320 mg of PVP-K30 polymer was added and stirred at 45-50° C. for 2 hours. The reaction mixture was distilled under vacuum at 60-65° C. The product was dried under vacuum at 55-60° C. to obtain 145 mg amorphous apixaban.

Example-16

7 gm of Apixaban was dissolved in 98 ml mixture of 70 ml of dichloromethane and 28 ml of methanol at 25-30° C. The content was filtered to remove insoluble particles. The clear filtrate was spray dried using Labultima LU222 Advance mini spray dryer to get 3.8 gm of Amorphous Apixaban under specified conditions as mentioned below.

| Sr. No. | Parameter | Conditions |
| --- | --- | --- |
| 1 | Feed Pump RPM | 12 RPM |
| 2 | Inlet temperature | 75° C. |
| 3 | Outlet temperature | 65° C. |
| 4 | Aspirator RPM | 99 RMP |
| 5 | Vacuum for conveying dry product | 130 mm Hg |
| 6 | Hot air supply | 2 Kg/cm$^2$ |

Figure 3:
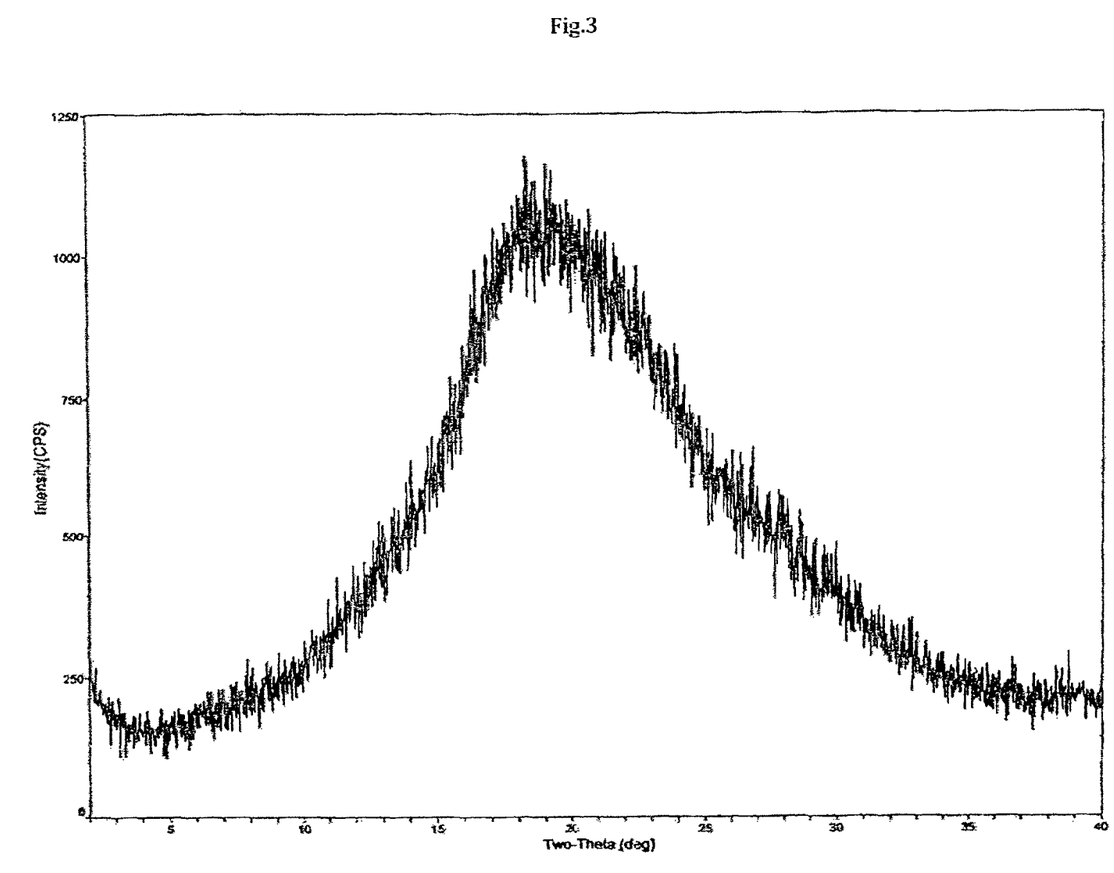
FIG. 3: Illustrates XRPD of amorphous Form of apixaban (I).

(XRD: FIG. 3).

While the present invention has been described in terms of its specific embodiments, certain modification and equivalents will be apparent to those skilled in art and the intended to be included within the scope of the invention.

We claim:

1. A crystalline Form N-1 of apixaban substantially free from one or more of: 1-(4-methoxyphenyl)-7-oxo-6-(4-(2-oxopiperidin-1-yl)phenyl)-4,5,6,7-tetrahydro-1H-pyrazolo[3,4-c]pyridine-3-carboxylic acid; 7-oxo-6-(4-(2-oxopiperidin-1-yl)phenyl)-1-phenyl-4,5,6,7-tetrahydro-1H-pyrazolo[3,4-c] pyridine-3-carboxamide; or methyl 1-(4-methoxyphenyl)-7-oxo-6-(4-(2-oxopiperidin-1-yl)phenyl)-4,5,6,7-tetrahydro-1H-pyrazolo[3,4-c]pyridine-3-carboxylate, relative to apixaban by area percentage of HPLC and having a mean particle size equal to or greater than 100 μm.

2. The crystalline Form N-1 of apixaban according to claim 1 having an X-ray powder diffraction pattern comprising peaks expressed in degrees 2θ (±0.2° 2θ) at 12.8°, 13.8°, 16.9°, 18.3°, 21.0°, 22.0°, and 26.8°±0.2 2θ.

3. A composition comprising crystalline Form N-1 of apixaban and one or more of 1-(4-methoxyphenyl)-7-oxo-6-(4-(2-oxopiperidin-1-yl)phenyl)-4,5,6,7-tetrahydro-1H-pyrazolo[3,4-c]pyridine-3-carboxylic acid; 7-oxo-6-(4-(2-oxopiperidin-1-yl)phenyl)-1-phenyl-4,5,6,7-tetrahydro-1H-pyrazolo[3,4-c]pyridine-3-carboxamide; or methyl 1-(4-methoxyphenyl)-7-oxo-6-(4-(2-oxo-piperidin-1-yl)phenyl)-4,5, 6,7-tetrahydro-1H-pyrazolo[3,4-c]pyridine-3-carboxylate in an amount relative to apixaban less than about 0.15% by weight by area percentage of HPLC.

4. The composition according to claim 3, wherein the apixaban has a purity of greater than or equal to 99% by weight, and 1-(4-methoxyphenyl)-7-oxo-6-(4-(2-oxopiperidin-1-yl)phenyl)-4,5,6,7-tetrahydro-1H-pyrazolo[3,4-c]pyridine-3-carboxylic acid present in an amount relative to apixaban less than about 0.10% by weight by area percentage of HPLC.

5. The composition according to claim 3, wherein the apixaban has a purity of greater than or equal to 99% by weight, and 7-oxo-6-(4-(2-oxopiperidin-1-yl)phenyl)-1-phenyl-4,5,6,7-tetrahydro-1H-pyrazolo[3,4-c]pyridine-3-carboxamide present in an amount relative to apixaban less than about 0.10% by weight by area percentage of HPLC.

6. The composition according to claim 3, wherein the apixaban has a purity of greater than or equal to 99% by weight, and methyl 1-(4-methoxyphenyl)-7-oxo-6-(4-(2-oxopiperidin-1-yl)phenyl)-4,5,6,7-tetrahydro-1H-pyrazolo[3,4-c]pyridine-3-carboxylate present in an amount relative to apixaban less than about 0.10% by weight by area percentage of HPLC.

7. A process for the preparation of the crystalline Form N-1 of apixaban according to claim 1, the process comprising:

(a) reacting (Z)-ethyl 2-chloro-2-(2-(4-methoxyphenyl)hydrazono)acetate of Formula (V) with 3-morpholino-1-(4-nitrophenyl)-5,6-dihydropyridin-2(1H)-one of Formula (VI) in one or more solvents in the presence of a base optionally in the presence of a phase transfer catalyst to obtain a compound of Formula (IVa);

(V)

(VI)

(IVa)

(b) treating the compound of Formula (IVa) with an acid to obtain a compound of Formula (IV);

(IV)

(c) reducing the compound of Formula (IV) with a reducing agent to obtain a compound of Formula (III);

(d) amidating the compound of Formula (III) with an amidating source in one or more solvents to obtain a compound of Formula (II);

(e) reacting the compound of Formula (II) with 5-chlorovalaroyl chloride in the presence of a base to obtain a compound of Formula (IIB) as a crystalline solid;

(f) cyclizing the compound of Formula (IIB) in the presence of a base in one or more solvents to obtain apixaban; and (g) crystallizing the apixaban in one or more solvents to obtain the crystalline Form N-1 of apixaban having a mean particle size equal to or greater than 100 μm.

8. The process according to claim 7, wherein the solvents in step (a) comprises one or more of water, methanol, ethanol, isopropanol, n-butanol, ethyl acetate, isopropyl acetate, butyl acetate, acetone, methylethyl ketone, methylisobutyl ketone, acetonitrile, dimethylformamide, dimethylacetamide, dimethylsulfoxide, N-methyl pyrrolidone, tetrahydrofuran, 2-methyl tetrahydrofuran, toluene, xylene, methylene dichloride, and ethylene dichloride or a mixture thereof.

9. The process according to claim 7, wherein the base in step (a) comprises one or more of sodium hydroxide, potassium hydroxide, lithium hydroxide, sodium carbonate, potassium carbonate, lithium carbonate, cesium carbonate, sodium bicarbonate, potassium bicarbonate, sodium hydride, potassium hydroxide, sodium methoxide, sodium ethoxide, potassium tert-butoxide, ammonia, TEA, DIPA, DEA, DIPEA, N-methyl morpholine, DBU, DABCO, and DBN.

10. The process according to claim 7, wherein the phase transfer catalyst comprises one or more of tetrabutyl ammonium bromide (TBAB), tetrabutyl ammonium iodide (TBAI), benzyl triethyl ammonium chloride (TEBAC), polyethylene Glycol (PEG-200, 400, 600, 800, 1000), crown ethers such as 12-crown-4, 15-crown-5, 18-crown-6, dibenzo-18-crown-6, and diaza-18-crown-6.

11. The process according to claim 7, wherein the acid in step (b) comprises one or more of hydrochloric acid, nitric acid, hydrobromic acid, sulfuric acid, acetic acid, and phosphoric acid.

12. The process according to claim 7, wherein the reducing agent in step (c) comprises one or more of Raney Nickel, Pd/C, Pt/C, Platinum oxide, Fe—HCl, Fe—NH$_4$Cl, Sn—HCl, and Na$_2$Sx.

13. The process according to claim 7, wherein the amidating source in step (d) comprises one or more of formamide selected from N-ethyl-formamide, N-methyl-formamide, and formamide; or ammonia.

14. The process according to claim 7, wherein the solvent in step (d) comprises one or more of alcohols selected from methanol, ethanol, isopropanol, and butanol; ketones selected from acetone, methyl ethyl ketone, and methyl isobutyl ketone; esters selected from ethyl acetate, isopropyl acetate, and butyl acetate.

15. The process according to claim 7, wherein the base in step (e) comprises one or more of sodium hydroxide, potassium hydroxide, lithium hydroxide, sodium carbonate, potassium carbonate, lithium carbonate, sodium bicarbonate, potassium bicarbonate, sodium hydride, potassium hydroxide, sodium methoxide, sodium ethoxide, potassium tert-butoxide, ammonia, TEA, DIPA, DEA, DIPEA, DBU, DABCO, and DBN.

16. The process according to claim 7, wherein the solvent in step (f) comprises one or more of dimethylformamide, dimethyl acetate, dimethylsulfoxide, N-methylpyrrolidone, acetonitrile, tetrahydrofuran, and 1,4-dioxane.

17. A pharmaceutical composition comprising crystalline Form N-1 of apixaban having a purity of greater than or equal to 99% by weight; one or more of 1-(4-methoxyphenyl)-7-oxo-6-(4-(2-oxopiperidin-1-yl)phenyl)-4,5,6,7-tetrahydro-1H-pyrazolo[3,4-c]pyridine-3-carboxylic acid; 7-oxo-6-(4-(2-oxopiperidin-1-yl)phenyl)-1-phenyl-4,5,6,7-tetrahydro-1H-pyrazolo[3,4-c]pyridine-3-carboxamide; or methyl 1-(4-methoxyphenyl)-7-oxo-6-(4-(2-oxopiperidin-1-yl)phenyl)-4,5,6,7-tetrahydro-1H-pyrazolo[3,4-c]pyridine-3-carboxylate in an amount relative to apixaban less than about 0.15% by weight by area percentage of HPLC; and one or more pharmaceutically acceptable excipients, diluents and carriers.

18. A pharmaceutical composition comprising crystalline form N-1 of apixaban having an X-ray powder diffraction pattern comprising peaks expressed in degrees 2θ (±0.2° 2θ) at 8.4°, 12.8°, 13.8°, 16.9°, 18.3°, 21.0°, 22.0°, 24.7°, 25.3°, 26.8° and 32.6°±0.2 2θ, having a mean particle size equal to or greater than 100 μm and one or more pharmaceutically acceptable excipients, diluents and carriers.

* * * * *